United States Patent
Donaghy et al.

(10) Patent No.: US 11,406,837 B2
(45) Date of Patent: Aug. 9, 2022

(54) DEFIBRILLATOR PROVIDING CARDIO PULMONARY RESUSCITATION FEEDBACK

(71) Applicant: HeartSine Technologies Limited, Belfast (GB)

(72) Inventors: Dymphna Mary Donaghy, County Donegal (IE); Johnny Houston Anderson, Holywood (IE); Olibhear Oisin Gerard McAlister, Belfast (GB); Hannah Louise Torney, Newtownabbey (GB); Adam Patrick Harvey, Hillsborough (GB)

(73) Assignee: Heartsine Technologies Limited, Belfast (GB)

( * ) Notice: Subject to any disclaimer, the term of this patent is extended or adjusted under 35 U.S.C. 154(b) by 346 days.

(21) Appl. No.: 16/798,765

(22) Filed: Feb. 24, 2020

(65) Prior Publication Data

US 2020/0269060 A1  Aug. 27, 2020

(30) Foreign Application Priority Data

Feb. 25, 2019 (GB) .................................... 1902526

(51) Int. Cl.
*A61N 1/00* (2006.01)
*A61N 1/39* (2006.01)
*A61H 31/00* (2006.01)
*A61B 5/08* (2006.01)

(52) U.S. Cl.
CPC ....... *A61N 1/39044* (2017.08); *A61H 31/005* (2013.01); *A61B 5/0809* (2013.01); *A61H 2201/10* (2013.01)

(58) Field of Classification Search
CPC .............. A61N 1/39044; A61H 31/005; A61H 2201/10; A61H 2201/5007; A61H 31/007; A61H 2201/1253; A61H 2201/5043; A61H 2201/5071; A61H 2201/5084; A61H 2230/04; A61H 2230/045; A61H 2230/08; A61H 2230/205; A61H 2230/207; A61H 2230/30; A61H 2230/82; A61H 31/00; A61H 31/004; A61B 5/0809; G09B 19/24; G16H 20/30
See application file for complete search history.

(56) References Cited

U.S. PATENT DOCUMENTS

2019/0224434 A1* 7/2019 Silver .................. A61N 1/3925
2021/0308002 A1* 10/2021 Donaghy ............... G16H 40/67

* cited by examiner

*Primary Examiner* — Scott M. Getzow (57) ABSTRACT

A defibrillator assesses cardio pulmonary resuscitation carried out on a subject and provides feedback. The defibrillator measures bio signals of the subject, determines when CPR is required and produces a start signal and determines and when CPR is no longer required and produces a stop signal. A measurement system measures compression signals during CPR chest compressions, a CPR assessment system receives the CPR start signal and the CPR stop signal and receives compression signals. The defibrillator uses the compression signals to establish a first CPR performance measurement, set a performance baseline of the person equal to the first CPR performance measurement of the person, compare the further CPR performance measurement of the person with the CPR performance baseline of the person, produce a feedback signal and set the CPR performance baseline of the person equal to the further CPR performance measurement of the person and return to earlier operations.

17 Claims, 2 Drawing Sheets

DEFIBRILLATOR PROVIDING CARDIO PULMONARY RESUSCITATION FEEDBACK

PRIORITY

The present application claims priority to United Kingdom application No. 1902526.1, filed Feb. 25, 2019, the contents of which is incorporated herein by reference in its entirety.

BACKGROUND OF THE INVENTION

1. Field of the Invention

The invention relates to a defibrillator providing cardio pulmonary resuscitation (CPR) feedback to a person during the performance of CPR on a subject.

2. Background

Various circumstances may arise when a defibrillator instructs a person to carry out CPR on a subject. CPR involves the compression of the subject's chest to cause the heart to pump blood around their circulatory system, primarily to provide oxygenated blood to the subject's heart and brain. If the compression of the chest is too shallow, then the heart will not pump sufficient oxygenated blood and the heart and brain tissue will start to die. For effective CPR, guidelines recommend a specific target depth of compression of the subject's chest. Typically, however, most people do not achieve this target depth. Defibrillators which provide feedback based on comparison of CPR performance of the person with a guideline-set target depth can discourage the person if they do not reach the target.

SUMMARY

It is an object of the present invention to provide a defibrillator which assesses CPR carried out by a person on a subject and provides CPR feedback to the person based on the person's CPR performance.

According to the disclosure there is provided a defibrillator which assesses cardio pulmonary resuscitation (CPR) carried out by a person on a subject and provides CPR feedback to the person, including:

a biosignal measurement system configured to measure biosignals of the subject, determine when CPR is required and produce a CPR start signal and determine and when CPR is to be ceased and produce a CPR stop signal, a CPR measurement system configured to measure compression signals during CPR chest compressions by the person, and a CPR assessment system connected to the biosignal measurement system to receive the CPR start signal and the CPR stop signal, connected to the CPR measurement system to receive compression signals. The CPR assessment system can be configured to perform the steps or operations including one or more of (in any order):

(i) receiving the CPR start signal and produce a first feedback signal, (ii) receiving compression signals measured during a first plurality of chest compressions by the person, (iii) using the compression signals to establish a first CPR performance measurement of the person, (iv) setting a CPR performance baseline of the person equal to the first CPR performance measurement of the person, (v) receiving compression signals measured during a further plurality of chest compressions by the person, (vi) using the compression signals to establish a further CPR performance measurement of the person, and (vii) comparing the further CPR performance measurement of the person with the CPR performance baseline of the person. A step (viii) can include, when the further CPR performance measurement of the person is greater than the CPR performance baseline of the person, producing a second feedback signal and set the CPR performance baseline of the person equal to the further CPR performance measurement of the person and going to step (x). Further steps can include (ix) when the further CPR performance measurement of the person is less than the CPR performance baseline of the person, producing a third feedback signal and go to step (x), (x) when the CPR stop signal is not received, returning to step (v), and (xi) when the CPR stop signal is received, producing a fourth feedback signal. The system can further include a feedback unit connected to the CPR assessment system and configured to receive the feedback signals and issue CPR feedback to the person.

BRIEF DESCRIPTION OF THE FIGURES

In order to describe the manner in which the above-recited and other advantages and features of the disclosure can be obtained, a more particular description of the principles briefly described above will be rendered by reference to specific embodiments thereof which are illustrated in the appended drawings. Understanding that these figures depict only exemplary embodiments of the disclosure and are not therefore to be considered to be limiting of its scope, the principles herein are described and explained with additional specificity and detail through the use of the accompanying drawings in which.

DETAILED DESCRIPTION

As noted above, effective CPR guidelines recommend a specific target depth of compression of the subject's chest. Because most people do not achieve this target depth, this disclosure introduces an improvement in defibrillators technology with respect to the feedback and how it can be provided to not discourage the person if they do not reach the target. The new structure of feedback can be based on comparison of a person's CPR performance during a number of CPR periods and can improve CPR performance.

According to the disclosure there is provided a defibrillator which assesses cardio pulmonary resuscitation (CPR) carried out by a person on a subject and provides CPR feedback to the person, including one or more of: a biosignal measurement system configured to measure biosignals of the subject, determine when CPR is required and produce a CPR start signal and determine and when CPR is to be ceased and produce a CPR stop signal, a CPR measurement system configured to measure compression signals during CPR chest compressions by the person, and a CPR assessment system connected to the biosignal measurement system to receive the CPR start signal and the CPR stop signal, connected to the CPR measurement system to receive compression signals. The system can be configured to perform one or more of the following steps or operations. The system can: (i) receive the CPR start signal and produce a first feedback signal, (ii) receive compression signals measured during a first plurality of chest compressions by the person, (iii) use the compression signals to establish a first CPR performance measurement of the person, (iv) set a CPR performance baseline of the person equal to the first CPR performance measurement of the person, (v) receive compression signals measured during a further plurality of chest compressions by the person, (vi) use the compression signals to establish a further CPR performance measurement of the person, (vii) compare the further CPR performance measurement of the person with the CPR performance baseline of the person, (viii) when the further CPR performance measurement of the person is greater than the CPR performance baseline of the person, produce a second feedback signal and set the CPR performance baseline of the person equal to the further CPR performance measurement of the person and go to step (x), (ix) when the further CPR performance measurement of the person is less than the CPR performance baseline of the person, produce a third feedback signal and go to step (x), (x) when the CPR stop signal is not received, return to step (v), and (xi) when the CPR stop signal is received, produce a fourth feedback signal.

The system can include a feedback unit connected to the CPR assessment system and configured to receive the feedback signals and issue CPR feedback to the person.

The defibrillator measures the CPR performance of the person during a plurality of CPR chest compressions and uses self-comparison of the person's CPR performance to provide appropriate CPR feedback.

Steps (viii) to (x) may be modified such that the system can: (viii) when the further CPR performance measurement is greater than the CPR performance baseline, produce the second feedback signal and set the CPR performance baseline equal to the further CPR performance measurement and go to step (x)(a), (ix) when the further CPR performance measurement is less than the CPR performance baseline, produce the third feedback signal and go to step (x)(b), (x)(a) when the CPR stop signal is not received, return to step (v), (x)(b) when the CPR stop signal is not received, wait for a plurality of chest compressions, return to step (v).

Steps (viii) to (x) may be modified such that the system can: (viii) when the further CPR performance measurement is greater than the CPR performance baseline, produce the second feedback signal and set the CPR performance baseline equal to the further CPR performance measurement and go to step (x)(a), (ix) when the further CPR performance measurement is less than the CPR performance baseline, produce the third feedback signal and go to step (x)(b), (x)(a) when the CPR stop signal is not received, wait for a plurality of chest compressions, return to step (v), (x)(b) when the CPR stop signal is not received, return to step (v).

Steps (viii) to (x) may be modified such that the system can: (viii) when the further CPR performance measurement is greater than the CPR performance baseline, produce the second feedback signal and set the CPR performance baseline equal to the further CPR performance measurement and go to step (x)(a), (ix) when the further CPR performance measurement is less than the CPR performance baseline, produce the third feedback signal and go to step (x)(b), (x)(a) when the CPR stop signal is not received, wait for a plurality of chest compressions, return to step (v), (x)(b) when the CPR stop signal is not received, wait for a plurality of chest compressions, return to step (v).

Steps (ii) to (iv) may be modified such that the system can: (ii) receive first compression signals measured during a first plurality of chest compressions by the person and at least second compression signals measured during a second plurality of chest compressions by the person, (iii) use the first compression signals to establish a first CPR performance measurement and use the at least second compression signals to establish an at least second CPR performance measurement, (iv) set a CPR performance baseline equal to the greater of the first CPR performance measurement and the at least second CPR performance measurement.

Steps (v) to (x) may be modified such that the system can: (v)(a) set a CPR counter equal to x, (v)(b) receive compression signals measured during a further plurality of chest compressions by the person, (vi) use the compression signals to establish a further CPR performance measurement, (vii) compare the further CPR performance measurement with the CPR performance baseline, (viii) when the further CPR performance measurement is greater than the CPR performance baseline, produce the second feedback signal, set the CPR performance baseline equal to the further CPR performance measurement and go to (x)(a), (ix)(a) when the further CPR performance measurement is less than the CPR performance baseline, when the CPR counter is not equal to zero, produce the third feedback signal, decrease the CPR counter by 1 and go to (x)(b), (ix)(b) when the further CPR performance measurement is less than the CPR performance baseline, when the CPR counter is equal to zero, produce the second feedback signal, decrease the CPR performance baseline and go to (x)(a), (x)(a) when the CPR stop signal is not received, return to step (v)(a), and (x)(b) when the CPR stop signal is not received, return to step (v)(b). Decreasing the CPR performance baseline may include setting the CPR performance baseline equal to the further CPR performance measurement. Decreasing the CPR performance baseline may include setting the CPR performance baseline equal to a greater of further CPR performance measurements.

Step (x)(a) may include when the CPR stop signal is not received, wait for a plurality of compressions and return to step (v)(a). Step (x)(b) may include when the CPR stop signal is not received, wait for a plurality of compressions and return to step (v)(b).

Step (ii) may be modified such that the system can: (ii)(a) set a CPR counter equal to x, (ii)(b) receive compression signals measured during a first plurality of chest compressions by the person, (ii)(c) receive a compression rate measured during the first plurality of chest compressions, (ii)(d) compare the measured compression rate with a minimum required compression rate, (ii)(e) when the measured compression rate is greater than the minimum required compression rate, go to step (iii), (ii)(f) when the measured compression rate is less than the minimum required compression rate, when the CPR counter is not equal to zero, decrease the CPR counter by 1, produce a fifth feedback signal and go to step (ii)(b), (ii)(g) when the measured compression rate is less than the minimum required compression rate, when the CPR counter is equal to zero, go to step (iii).

Step (ii)(f) may include the system being configured, when the measured compression rate is less than the minimum required compression rate, when the CPR counter is not equal to zero, to decrease the CPR counter by 1, produce a fifth feedback signal, wait for a plurality of compressions and go to step (ii)(b).

Alternatively, step (ii) may be modified such that the system can: (ii)(a) set a CPR counter equal to x, (ii)(b) receive compression signals measured during a first plurality of chest compressions by the person, (ii)(c) receive a compression rate measured during the first plurality of chest compressions, (ii)(d) compare the measured compression rate with a maximum required compression rate, (ii)(e) when the measured compression rate is less than the maximum required compression rate, go to step (iii), (ii)(f) when the measured compression rate is greater than the maximum required compression rate, when the CPR counter is not equal to zero, decrease the CPR counter by 1, produce a sixth feedback signal and go to step (ii)(b), (ii)(g) when the measured compression rate is greater than the maximum required compression rate, when the CPR counter is equal to zero, go to step (iii).

Step (ii)(f) may be modified such that the system can, when the measured compression rate is greater than the maximum required compression rate, when the CPR counter is not equal to zero, decrease the CPR counter by 1, produce a sixth feedback signal, wait for a plurality of compressions and go to step (ii)(b).

Alternatively, step (ii) may be modified such that the system can: (ii)(a) set a CPR counter equal to x, (ii)(b) receive compression signals measured during a first plurality of chest compressions by the person, (ii)(c) receive a compression rate measured during the first plurality of chest compressions, (ii)(d) compare the measured compression rate with a minimum required compression rate and a maximum required compression rate, (ii)(e) when the measured compression rate is greater than the minimum required compression rate and when the measured compression rate is less than the maximum required compression rate, go to step (iii), (ii)(f) when the measured compression rate is less than the minimum required compression rate, when the CPR counter is not equal to zero, decrease the CPR counter by 1, produce a fifth feedback signal and go to step (ii)(b), (ii)(g) when the measured compression rate is less than the minimum required compression rate, when the CPR counter is equal to zero, go to step (iii), (ii)(h) when the measured compression rate is greater than the maximum required compression rate, when the CPR counter is not equal to zero, decrease the CPR counter by 1, produce a sixth feedback signal and go to step (ii)(b), and (ii)(i) when the measured compression rate is greater than the maximum required compression rate, when the CPR counter is equal to zero, go to step (iii).

Step (ii)(f) may include when the measured compression rate is less than the minimum required compression rate, when the CPR counter is not equal to zero, decrease the CPR counter by 1, produce a fifth feedback signal, wait for a plurality of compressions and go to step (ii)(b).

Step (ii)(h) may be modified such that the system can, when the measured compression rate is greater than the maximum required compression rate, when the CPR counter is not equal to zero, decrease the CPR counter by 1, produce a sixth feedback signal, wait for a plurality of compressions and go to step (ii)(b).

Step (v) may be modified such that the system can: (v)(a) set a CPR counter equal to x, (v)(b) receive compression signals measured during a further plurality of chest compressions by the person, (v)(c) receive a compression rate measured during the further plurality of chest compressions, (v)(d) compare the measured compression rate with a minimum required compression rate, (v)(e) when the measured compression rate is greater than the minimum required compression rate, go to step (vi), (v)(f) when the measured compression rate is less than the minimum required compression rate, when the CPR counter is not equal to zero, decrease the CPR counter by 1, produce a fifth feedback signal and go to step (v)(b), (v)(g) when the measured compression rate is less than the minimum required compression rate, when the CPR counter is equal to zero, go to step (vi).

Step (v)(f) may be modified such that system can, when the measured compression rate is less than the minimum required compression rate, when the CPR counter is not equal to zero, decrease the CPR counter by 1, produce a fifth feedback signal, wait for a plurality of compressions and go to step (v)(b).

Alternatively, step (v) may be modified such that the system can: (v)(a) set a CPR counter equal to x, (v)(b) receive compression signals measured during a further plurality of chest compressions by the person, (v)(c) receive a compression rate measured during the further plurality of chest compressions, (v)(d) compare the measured compression rate with a maximum required compression rate, (v)(e) when the measured compression rate is less than the maximum required compression rate, go to step (vi), (v)(f) when the measured compression rate is greater than the maximum required compression rate, when the CPR counter is not equal to zero, decrease the CPR counter by 1, produce a sixth feedback signal and go to step (v)(b), (v)(g) when the measured compression rate is greater than the maximum required compression rate, when the CPR counter is equal to zero, go to step (vi).

Step (v)(f) may be modified such that the system can, when the measured compression rate is greater than the maximum required compression rate, when the CPR counter is not equal to zero, decrease the CPR counter by 1, produce a sixth feedback signal, wait for a plurality of compressions and go to step (v)(b).

Alternatively, step (v) may be modified such that the system can: (v)(a) set a CPR counter equal to x, (v)(b) receive compression signals measured during a further plurality of chest compressions by the person, (v)(c) receive a compression rate measured during the further plurality of chest compressions, (v)(d) compare the measured compression rate with a minimum required compression rate and a maximum required compression rate, (v)(e) when the measured compression rate is greater than the minimum required compression rate and when the measured compression rate is less than the maximum required compression rate, go to step (vi), (v)(f) when the measured compression rate is less than the minimum required compression rate, when the CPR counter is not equal to zero, decrease the CPR counter by 1, produce a fifth feedback signal and go to step (v)(b), (v)(g) when the measured compression rate is less than the minimum required compression rate, when the CPR counter is equal to zero, go to step (vi), (v)(h) when the measured compression rate is greater than the maximum required compression rate, when the CPR counter is not equal to zero, decrease the CPR counter by 1, produce a sixth feedback signal and go to step (v)(b), (v)(i) when the measured compression rate is greater than the maximum required compression rate, when the CPR counter is equal to zero, go to step (vi).

Step (v)(f) may include when the measured compression rate is less than the minimum required compression rate, when the CPR counter is not equal to zero, decrease the CPR counter by 1, produce a fifth feedback signal, wait for a plurality of compressions and go to step (v)(b).

Step (v)(h) may include when the measured compression rate is greater than the maximum required compression rate, when the CPR counter is not equal to zero, decrease the CPR counter by 1, produce a sixth feedback signal, wait for a plurality of compressions and go to step (v)(b).

The CPR assessment system may be configured to perform a step (iii)(a) after step (iii) comprising comparing the first CPR performance measurement of the person with a minimum CPR performance measurement, when the first CPR performance measurement is greater than the minimum CPR performance measurement, going to step (iv), when the first CPR performance measurement is less than the minimum CPR performance measurement, producing the third prompt signal and returning to step (ii).

Step (iii)(a) may include when the first CPR performance measurement is less than the minimum CPR performance measurement, producing the third prompt signal, waiting for a plurality of compressions and returning to step (ii).

The CPR assessment system may be configured to perform a step (iii)(b) after step (iii)(a) comprising comparing the first CPR performance measurement of the person with a maximum CPR performance measurement, when the first CPR performance measurement is less than the maximum CPR performance measurement, going to step (iv), when the first CPR performance measurement is greater than the maximum CPR performance measurement, producing a seventh prompt signal and returning to step (ii).

Step (iii)(b) may be modified such that the system can, when the first CPR performance measurement is greater than the maximum CPR performance measurement, produce a seventh prompt signal, wait for a plurality of compressions and return to step (ii).

The CPR assessment system may be configured to perform a step (vi)(a) after step (vi) comprising comparing the further CPR performance measurement of the person with a minimum CPR performance measurement, when the further CPR performance measurement is greater than the minimum CPR performance measurement, going to step (vii), when the further CPR performance measurement is less than the minimum CPR performance measurement, producing the third prompt signal and returning to step (v).

Step (vi)(a) may be modified such that the system can, when the further CPR performance measurement is less than the minimum CPR performance measurement, produce the third prompt signal, wait for a plurality of compressions and return to step (v).

The CPR assessment system may be configured to perform a step (vi)(b) after step (vi)(a) comprising comparing the further CPR performance measurement of the person with a maximum CPR performance measurement, when the further CPR performance measurement is less than the maximum CPR performance measurement, going to step (vii), when the further CPR performance measurement is greater than the maximum CPR performance measurement, producing the seventh prompt signal and returning to step (v).

Step (vi)(b) may be modified such that the system can, when the further CPR performance measurement is greater than the maximum CPR performance measurement, produce the seventh prompt signal, wait for a plurality of compressions and return to step (v).

The minimum CPR performance measurement and the maximum CPR performance measurement may include extremes of a pre-defined acceptable range of CPR performance.

The first CPR performance measurement may include a measurement tolerance. The further CPR performance measurement may include a measurement tolerance. The measurement tolerance may be approximately 10%.

The CPR measurement system may measure compression signals during the first plurality of chest compressions by the person and during the further plurality of chest compressions by the person comprising displacement signals of the chest of the subject during the chest compressions. The displacement signals of the chest of the subject may be measured using an accelerometer positioned on the chest of the subject. The CPR assessment system may establish the first CPR performance measurement of the person by measuring and averaging an amplitude of the displacement signals over the first plurality of chest compressions by the person. The CPR assessment system may establish the further CPR performance measurement of the person by measuring and averaging an amplitude of the displacement signals over the further plurality of chest compressions by the person.

The CPR measurement system may measure compression signals during the first plurality of chest compressions by the person and during the further plurality of chest compressions by the person comprising compression-sensitive physiological signals of the subject during the chest compressions. The compression-sensitive physiological signals of the subject may include any of thoracic impedance signals, end tidal $CO_2$ signals, blood pressure signals, $SpO_2$ signals, $rSO_2$ signals, electrocardiogram signals. The CPR assessment system may establish the first CPR performance measurement of the person by measuring and averaging an amplitude of the compression-sensitive physiological signals of the subject over the first plurality of chest compressions by the person. The CPR assessment system may establish the further CPR performance measurement of the person by measuring and averaging an amplitude of the compression-sensitive physiological signals of the subject over the further plurality of chest compressions by the person.

An increase in the average amplitude of the compression-sensitive physiological signals of the subject between the first and further plurality of chest compressions by the person will indicate an improvement of the CPR performance of the person. A decrease in the average amplitude of the compression-sensitive physiological signals of the subject between the first and further plurality of chest compressions by the person will indicate a degradation of the CPR performance of the person.

The CPR measurement system may measure compression rates during the chest compressions by the person on the subject.

The feedback unit may receive the first feedback signal and issue CPR feedback in the form of a 'Start CPR and Push Hard' instruction to the person. The feedback unit may receive the second feedback signal and issue CPR feedback in the form of a 'Keep Going' instruction to the person. The feedback unit may receive the third feedback signal and issue CPR feedback in the form of a 'Push Harder' instruction to the person. The feedback unit may receive the fourth feedback signal and issue CPR feedback in the form of a 'Stop CPR' instruction to the person. The feedback unit may receive the fifth feedback signal and issue CPR feedback in the form of a 'Push Faster' instruction to the person. The feedback unit may receive the sixth feedback signal and issue CPR feedback in the form of a 'Push Slower' instruction to the person. The feedback unit may receive the seventh feedback signal and issue CPR feedback in the form of a 'Push Softer' instruction to the person.

Figure 1:
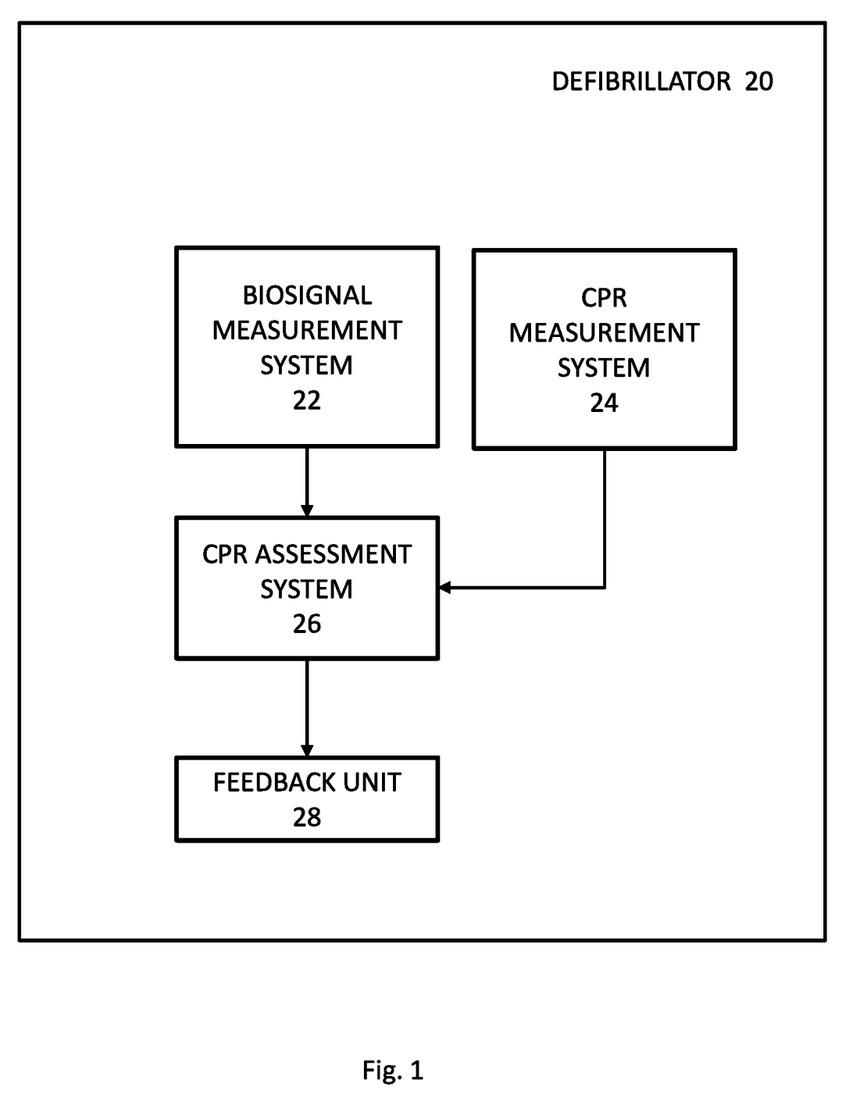
FIG. 1 is a schematic representation of a defibrillator according to the disclosure.

Referring to FIG. 1, the defibrillator 20 can include a biosignal measurement system 22, a CPR measurement system 24, a CPR assessment system 26 and a feedback unit 28. The defibrillator 20 assesses CPR carried out by a person (not shown) on a subject (not shown) and provides CPR feedback to the person.

It will be appreciated that the defibrillator 20 will include other elements such as an activation mechanism, a biosignal processing system, defibrillation shock generation circuitry, a power source and a sensing unit which is adapted to be attached to the subject.

The bio signal measurement system 22 is connected to the sensing unit and is configured to measure bio signals of the subject, in this embodiment, ECG biosignals. An algorithm uses the ECG biosignals to determine if the subject is exhibiting a condition which requires a defibrillation shock or a condition which requires CPR. When CPR is required, the biosignal measurement system 22 is configured to produce a CPR start signal. When CPR is to be ceased, the biosignal measurement system 22 is configured to produce a CPR stop signal.

In this embodiment, the CPR measurement system 24 is connected to the sensing unit and measures compression signals during chest compressions by the person. In this embodiment, the compression signals include compression-sensitive physiological signals consisting of thoracic impedance signals of the subject. The CPR measurement system 24 also measures compression rates during chest compressions by the person.

It will be appreciated that other compression-sensitive physiological signals can be used such as any of end tidal $CO_2$ signals, blood pressure signals, $SpO_2$ signals, $rSO_2$ signals, electrocardiogram signals. It will also be appreciated that the CPR measurement system could use other methods of measuring the compression signals, such as measurement of displacement signals of the chest of the subject during the chest compressions by the person.

The CPR assessment system 26 is connected to the biosignal measurement system 22 to receive the CPR start signal and the CPR stop signal. On receipt of the CPR start signal, the CPR assessment system 26 receives compression signals and commences assessment of CPR performance by the person on the subject over multiple pluralities of chest compressions. This includes performance of a number of steps, described below with reference to FIG. 2. On receipt of the CPR stop signal, the CPR assessment system 26 ceases assessment of CPR performance by the person on the subject.

The CPR assessment system 26 is connected to the CPR measurement system 24 and receives compression signals indicative of chest compressions comprising the thoracic impedance signals and uses these to assess CPR performance of the person over the multiple pluralities of chest compressions carried out by the person on the subject. The CPR assessment system 26 establishes CPR performance measurements of the person by measuring and averaging amplitudes of the thoracic impedance signals over each plurality of chest compressions by the person.

During assessment of the CPR performance of the person, the CPR assessment system 26 produces various feedback signals. The feedback unit 28 is connected to the CPR assessment system 26 and is configured to receive the feedback signals and issue CPR feedback to the person.

Figure 2:
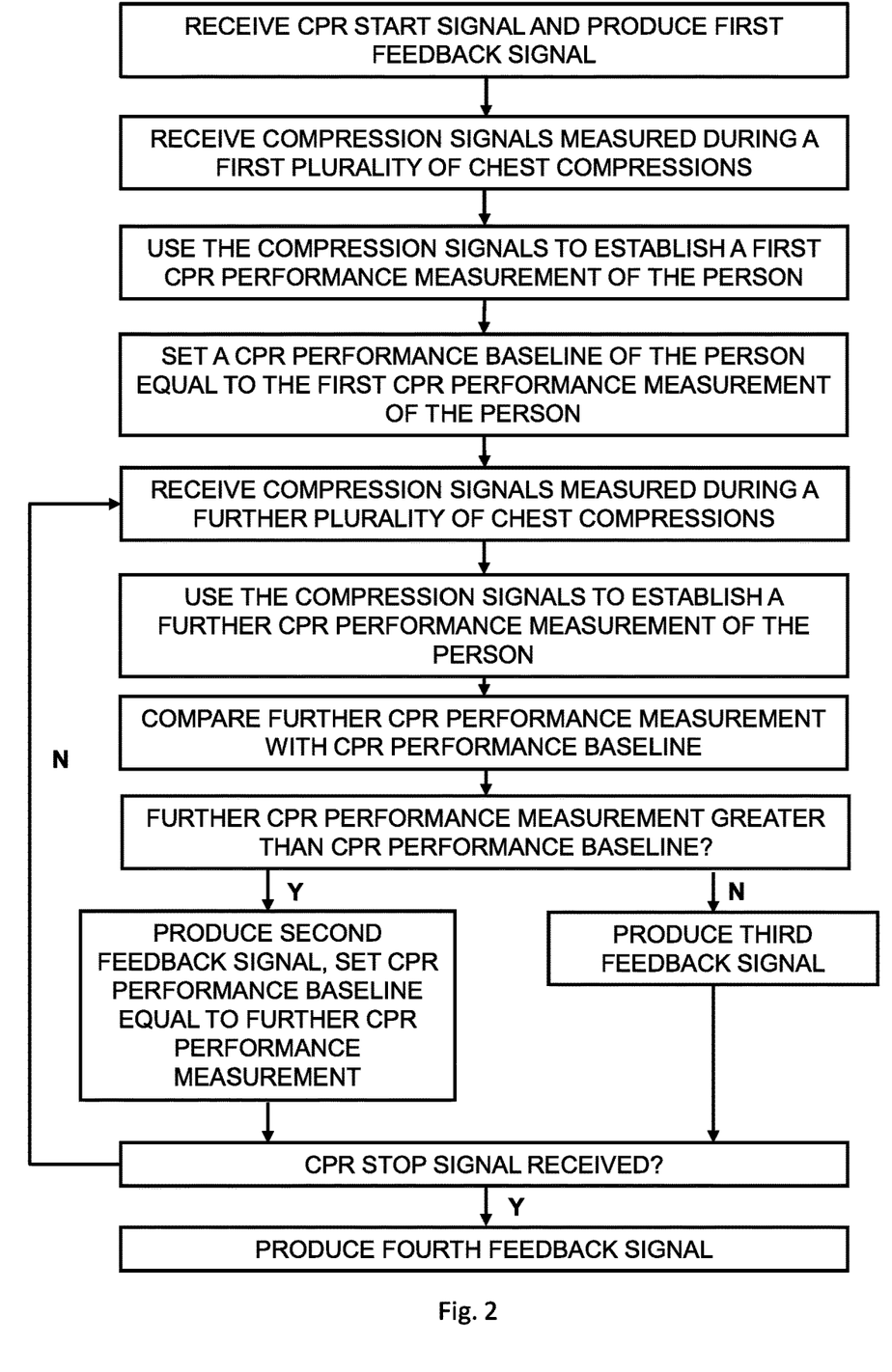
FIG. 2 is a flowchart of steps carried out by a CPR assessment system of the defibrillator of FIG. 1.

Referring to FIG. 2, the steps performed by the CPR assessment system 26 of the defibrillator 20 of FIG. 1 will be described.

On receipt of the CPR start signal, the CPR assessment system 26 produces a first feedback signal. This is received by the feedback unit 28, which issues CPR feedback in the form of a 'Start CPR and Push Hard' instruction, to the person carrying out CPR on the subject.

The CPR assessment system 26 then receives compression signals measured by the CPR measurement system 24 during a first plurality of chest compressions and uses the compression signals to establish a first CPR performance measurement of the person. A CPR performance baseline of the person is then set to be equal to the first CPR performance measurement of the person.

The CPR assessment system 26 then receives compression signals measured by the CPR measurement system 24 during a further plurality of chest compressions and uses the compression signals to establish a further CPR performance measurement of the person.

The CPR assessment system 26 then compares the further CPR performance measurement of the person with the CPR performance baseline of the person. When the further CPR performance measurement is greater than the CPR performance baseline, the CPR assessment system 26 produces a second feedback signal and sets the CPR performance baseline equal to the further CPR performance measurement. The feedback unit 28 receives the second feedback signal and issues CPR feedback in the form of a 'Keep Going' instruction to the person carrying out CPR on the subject. This instruction is intended to encourage the person to continue applying chest compressions with the same force.

When the further CPR performance measurement of the person is less than the CPR performance baseline of the person, the CPR assessment system 26 produces a third feedback signal. The feedback unit 28 receives the third feedback signal and issues CPR feedback in the form of a 'Push Harder' instruction to the person carrying out CPR on the subject. This instruction is intended to encourage the person to apply more force in the chest compressions.

The CPR assessment system 26 then checks for receipt of the CPR stop signal from the biosignal measurement system 22. When the CPR stop signal has not been received, the CPR assessment system 26 returns to the step of receiving compression signals during a further plurality of chest compressions by the person. When the CPR stop signal is received, the CPR assessment system 26 produces a fourth feedback signal. The feedback unit 28 receives the fourth feedback signal and issues CPR feedback in the form of a 'Stop CPR' instruction to the person carrying out CPR on the subject.

Various modifications may be made to the steps performed by the CPR assessment system 26.

Steps (viii) to (x) may be modified such that the system can: (viii) when the further CPR performance measurement is greater than the CPR performance baseline, produce a second feedback signal and set the CPR performance baseline equal to the further CPR performance measurement and go to step (x)(a), (ix) when the further CPR performance measurement is less than the CPR performance baseline, produce a third feedback signal and go to step (x)(b), (x)(a) when the CPR stop signal is not received, return to step (v), (x)(b) when the CPR stop signal is not received, wait for a plurality of chest compressions, return to step (v).

This allows the person performing the CPR a number of chest compressions to bring their CPR performance back up to the baseline level assessed during the first plurality of chest compressions.

Steps (viii) to (x) may be modified such that the system can: (viii) when the further CPR performance measurement is greater than the CPR performance baseline, produce the second feedback signal and set the CPR performance baseline equal to the further CPR performance measurement and go to step (x)(a), (ix) when the further CPR performance measurement is less than the CPR performance baseline, produce the third feedback signal and go to step (x)(b), (x)(a) when the CPR stop signal is not received, wait for a plurality of chest compressions, return to step (v), (x)(b) when the CPR stop signal is not received, return to step (v).

Steps (viii) to (x) may be modified such that the system can: (viii) when the further CPR performance measurement is greater than the CPR performance baseline, produce the second feedback signal and set the CPR performance baseline equal to the further CPR performance measurement and go to step (x)(a), (ix) when the further CPR performance measurement is less than the CPR performance baseline, produce the third feedback signal and go to step (x)(b), (x)(a) when the CPR stop signal is not received, wait for a plurality of chest compressions, return to step (v), (x)(b) when the CPR stop signal is not received, wait for a plurality of chest compressions, return to step (v).

Steps (ii) to (iv) may be modified such that the system can: (ii) receive first compression signals measured during a first plurality of chest compressions and at least second compression signals measured during a second plurality of chest compressions, (iii) use the first compression signals to establish a first CPR performance measurement of the person and use the at least second compressions signals to establish an at least second CPR performance measurement of the person, (iv) set a CPR performance baseline equal to the greater of the first CPR performance measurement and the at least second CPR performance measurement.

Steps (v) to (x) may be modified such that the system can: (v)(a) set a CPR counter equal to x, (v)(b) receive compression signals measured during a further plurality of chest compressions, (vi) use the compression signals to establish a further CPR performance measurement, (vii) compare the further CPR performance measurement with the CPR performance baseline, (viii) when the further CPR performance measurement is greater than the CPR performance baseline, produce the second feedback signal, set the CPR performance baseline equal to the further CPR performance measurement and go to (x)(a), (ix)(a) when the further CPR performance measurement is less than the CPR performance baseline, when the CPR counter is not equal to zero, produce the third feedback signal, decrease the CPR counter by 1 and go to (x)(b), (ix)(b) when the further CPR performance measurement is less than the CPR performance baseline, when the CPR counter is equal to zero, produce the second feedback signal, decrease the CPR performance baseline and go to (x)(a), (x)(a) when the CPR stop signal is not received, return to step (v)(a), and (x)(b) when the CPR stop signal is not received, return to step (v)(b).

Decreasing the CPR performance baseline may include setting the CPR performance baseline equal to the further CPR performance measurement. Decreasing the CPR performance baseline may include setting the CPR performance baseline equal to a greater of further CPR performance measurements.

Step (x)(a) may cause the system, when the CPR stop signal is not received, to wait for a plurality of compressions and return to step (v)(a). Step (x)(b) may include when the CPR stop signal is not received, waiting for a plurality of compressions and return to step (v)(b). Step (ii) may be modified such that the system can: (ii)(a) set a CPR counter equal to x, (ii)(b) receive compression signals measured during a first plurality of chest compressions, (ii)(c) receive a compression rate measured during the first plurality of chest compressions, (ii)(d) compare the measured compression rate with a minimum required compression rate, (ii)(e) when the measured compression rate is greater than the minimum required compression rate, go to step (iii), (ii)(f) when the measured compression rate is less than the minimum required compression rate, when the CPR counter is not equal to zero, decrease the CPR counter by 1, produce a fifth feedback signal and go to step (ii)(b), (ii)(g) when the measured compression rate is less than the minimum required compression rate, when the CPR counter is equal to zero, go to step (iii).

Step (ii)(f) may include when the measured compression rate is less than the minimum required compression rate, when the CPR counter is not equal to zero, decrease the CPR counter by 1, produce a fifth feedback signal, wait for a plurality of compressions and go to step (ii)(b). Alternatively, step (ii) may be modified such that the system can: (ii)(a) set a CPR counter equal to x, (ii)(b) receive compression signals measured during a first plurality of chest compressions, (ii)(c) receive a compression rate measured during the first plurality of chest compressions, (ii)(d) compare the measured compression rate with a maximum required compression rate, (ii)(e) when the measured compression rate is less than the maximum required compression rate, go to step (iii), (ii)(f) when the measured compression rate is greater than the maximum required compression rate, when the CPR counter is not equal to zero, decrease the CPR counter by 1, produce a sixth feedback signal and go to step (ii)(b), (ii)(g) when the measured compression rate is greater than the maximum required compression rate, when the CPR counter is equal to zero, go to step (iii).

Step (ii)(f) may include the system, when the measured compression rate is greater than the maximum required compression rate, when the CPR counter is not equal to zero, decreasing the CPR counter by 1, produce a sixth feedback signal, waiting for a plurality of compressions and going to step (ii)(b).

Alternatively, step (ii) may be modified such that the system can: (ii)(a) set a CPR counter equal to x, (ii)(b) receive compression signals measured during a first plurality of chest compressions, (ii)(c) receive a compression rate measured during the first plurality of chest compressions, (ii)(d) compare the measured compression rate with a minimum required compression rate and a maximum required compression rate, (ii)(e) when the measured compression rate is greater than the minimum required compression rate and when the measured compression rate is less than the maximum required compression rate, go to step (iii), (ii)(f) when the measured compression rate is less than the minimum required compression rate, when the CPR counter is not equal to zero, decrease the CPR counter by 1, produce a fifth feedback signal and go to step (ii)(b), (ii)(g) when the measured compression rate is less than the minimum required compression rate, when the CPR counter is equal to zero, go to step (iii), (ii)(h) when the measured compression rate is greater than the maximum required compression rate, when the CPR counter is not equal to zero, decrease the CPR counter by 1, produce a sixth feedback signal and go to step (ii)(b), (ii)(i) when the measured compression rate is greater than the maximum required compression rate, when the CPR counter is equal to zero, go to step (iii).

Step (ii)(f) may include when the measured compression rate is less than the minimum required compression rate, when the CPR counter is not equal to zero, decrease the CPR counter by 1, producing a fifth feedback signal, waiting for a plurality of compressions and going to step (ii)(b).

Step (ii)(h) may include when the measured compression rate is greater than the maximum required compression rate, when the CPR counter is not equal to zero, decreasing the CPR counter by 1, producing a sixth feedback signal, waiting for a plurality of compressions and going to step (ii)(b).

Step (v) may be modified such that the system can: (v)(a) set a CPR counter equal to x, (v)(b) receive compression signals measured during a further plurality of chest compressions, (v)(c) receive a compression rate measured during the further plurality of chest compressions, (v)(d) compare the measured compression rate with a minimum required compression rate, (v)(e) when the measured compression rate is greater than the minimum required compression rate, go to step (vi), (v)(f) when the measured compression rate is less than the minimum required compression rate, when the CPR counter is not equal to zero, decrease the CPR counter by 1, produce a fifth feedback signal and go to step (v)(b), (v)(g) when the measured compression rate is less than the minimum required compression rate, when the CPR counter is equal to zero, go to step (vi).

Step (v)(f) may include when the measured compression rate is less than the minimum required compression rate, when the CPR counter is not equal to zero, decrease the CPR counter by 1, produce a fifth feedback signal, wait for a plurality of compressions and go to step (v)(b). Alternatively, step (v) may be modified such that the system can: (v)(a) set a CPR counter equal to x, (v)(b) receive compression signals measured during a further plurality of chest compressions, (v)(c) receive a compression rate measured during the further plurality of chest compressions, (v)(d) compare the measured compression rate with a maximum required compression rate, (v)(e) when the measured compression rate is less than the maximum required compression rate, go to step (vi), (v)(f) when the measured compression rate is greater than the maximum required compression rate, when the CPR counter is not equal to zero, decrease the CPR counter by 1, produce a sixth feedback signal and go to step (v)(b), (v)(g) when the measured compression rate is greater than the maximum required compression rate, when the CPR counter is equal to zero, go to step (vi).

Step (v)(f) may be modified such that the system can, when the measured compression rate is greater than the maximum required compression rate, when the CPR counter is not equal to zero, decrease the CPR counter by 1, produce a sixth feedback signal, wait for a plurality of compressions and go to step (v)(b).

Alternatively, step (v) may be modified such that the system can: (v)(a) set a CPR counter equal to x, (v)(b) receive compression signals measured during a further plurality of chest compressions, (v)(c) receive a compression rate measured during the further plurality of chest compressions, (v)(d) compare the measured compression rate with a minimum required compression rate and a maximum required compression rate, (v)(e) when the measured compression rate is greater than the minimum required compression rate and when the measured compression rate is less than the maximum required compression rate, go to step (vi), (v)(f) when the measured compression rate is less than the minimum required compression rate, when the CPR counter is not equal to zero, decrease the CPR counter by 1, produce a fifth feedback signal and go to step (v)(b), (v)(g) when the measured compression rate is less than the minimum required compression rate, when the CPR counter is equal to zero, go to step (vi), (v)(h) when the measured compression rate is greater than the maximum required compression rate, when the CPR counter is not equal to zero, decrease the CPR counter by 1, produce a sixth feedback signal and go to step (v)(b), (v)(i) when the measured compression rate is greater than the maximum required compression rate, when the CPR counter is equal to zero, go to step (vi).

Step (v)(f) may include when the measured compression rate is less than the minimum required compression rate, when the CPR counter is not equal to zero, decrease the CPR counter by 1, produce a fifth feedback signal, wait for a plurality of compressions and go to step (v)(b).

Step (v)(h) may include when the measured compression rate is greater than the maximum required compression rate, when the CPR counter is not equal to zero, decrease the CPR counter by 1, produce a sixth feedback signal, wait for a plurality of compressions and go to step (v)(b).

The minimum required compression rate may include approximately 100 compressions per minute. The feedback unit 28 may receive the fifth feedback signal and issue CPR feedback in the form of a 'Push Faster' instruction to the person carrying out CPR on the subject.

The maximum required compression rate may include approximately 120 compressions per minute. The feedback unit 28 may receive the sixth feedback signal and issue CPR feedback in the form of a 'Push Slower' instruction to the person carrying out CPR on the subject.

The CPR assessment system 26 may be configured to perform a step (iii)(a) after step (iii) comprising comparing the first CPR performance measurement with a minimum CPR performance measurement, when the first CPR performance measurement is greater than the minimum CPR performance measurement, going to step (iv), when the first CPR performance measurement is less than the minimum CPR performance measurement, producing the third prompt signal and returning to step (ii).

Step (iii)(a) may include, when the first CPR performance measurement is less than the minimum CPR performance measurement, producing the third prompt signal, waiting for a plurality of compressions and returning to step (ii).

The CPR assessment system 26 may be configured to perform a step (iii)(b) after step (iii)(a) including comparing the first CPR performance measurement with a maximum CPR performance measurement, when the first CPR performance measurement is less than the maximum CPR performance measurement go to step (iv), when the first CPR performance measurement is greater than the maximum CPR performance measurement, producing a seventh prompt signal and returning to step (ii).

Step (iii)(b) may include the system being configured, when the first CPR performance measurement is greater than the maximum CPR performance measurement, to produce a seventh prompt signal, wait for a plurality of compressions and return to step (ii).

The feedback unit 28 may receive the seventh feedback signal and issue CPR feedback in the form of a 'Push Softer' instruction to the person carrying out CPR on the subject.

The CPR assessment system 26 may be configured to perform a step (vi)(a) after step (vi) including comparing the further CPR performance measurement with a minimum CPR performance measurement, when the further CPR performance measurement is greater than the minimum CPR performance measurement, going to step (vii), when the further CPR performance measurement is less than the minimum CPR performance measurement, producing the third prompt signal and returning to step (v).

Step (vi)(a) may include when the further CPR performance measurement is less than the minimum CPR performance measurement, producing the third prompt signal, waiting for a plurality of compressions and returning to step (v).

The CPR assessment system 26 may be configured to perform a step (vi)(b) after step (vi)(a) including comparing the further CPR performance measurement with a maximum CPR performance measurement, when the further CPR performance measurement is less than the maximum CPR performance measurement, going to step (vii), when the further CPR performance measurement is greater than the maximum CPR performance measurement, producing the seventh prompt signal and returning to step (v).

Step (vi)(b) may be modified such that the system can, when the further CPR performance measurement is greater than the maximum CPR performance measurement, produce a seventh prompt signal, wait for a plurality of compressions and return to step (v).

It can be seen that the CPR assessment system of the defibrillator will repeatedly compare subsequent CPR performance of the person with previous CPR performance of the person, i.e. perform a 'CPR performance self-comparison'. Adaptive CPR feedback is then provided to the person, i.e. CPR feedback adapted according to the result of the CPR performance comparison.

The defibrillator 20 can includes computing system architecture including various components in electrical communication with each other using a connection in accordance with various embodiments. For example, the system can include components in electrical communication with each other using a connection, such as a bus. A processing unit (CPU or processor) and a system connection could couple various system components including the system memory, such as read only memory (ROM) and random access memory (RAM), to the processor. The system can include a cache of high-speed memory connected directly with, in close proximity to, or integrated as part of the processor. The system can copy data from the memory and/or the storage device to the cache for quick access by the processor. These and other modules can control or be configured to control the processor to perform various actions. Other system memory may be available for use as well. The memory can include multiple different types of memory with different performance characteristics. The processor can include any general purpose processor and a hardware or software service, such as different services or modules stored in storage device, configured to control the processor as well as a special-purpose processor where software instructions are incorporated into the actual processor design. The processor may be a completely self-contained computing system, containing multiple cores or processors, a bus, memory controller, cache, etc. A multi-core processor may be symmetric or asymmetric.

To enable user interaction with the defibrillator, an input device can represent any number of input mechanisms, such as a microphone for speech, a touch-sensitive screen for gesture or graphical input, keyboard, mouse, motion input, speech and so forth. An output device can also be one or more of a number of output mechanisms known to those of skill in the art. In some instances, multimodal systems can enable a user to provide multiple types of input to communicate with the device. The communications interface can generally govern and manage the user input and system output. There is no restriction on operating on any particular hardware arrangement and therefore the basic features here may easily be substituted for improved hardware or firmware arrangements as they are developed.

Storage device is a non-volatile memory and can be a hard disk or other types of computer readable media which can store data that are accessible by a computer, such as magnetic cassettes, flash memory cards, solid state memory devices, digital versatile disks, cartridges, random access memories (RAMs), read only memory (ROM), and hybrids thereof.

The storage device can include services or modules for controlling the processor. Other hardware or software modules are contemplated. The storage device can be connected to the system connection. In one aspect, a hardware module that performs a particular function can include the software component stored in a computer-readable medium in connection with the necessary hardware components, such as the processor, a connection, an output device, and so forth, to carry out the function.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se. In one example, using a protocol such as Bluetooth, the two devices may communicate directly with each other to manage the try-on session.

Methods according to the above-described examples can be implemented using computer-executable instructions that are stored or otherwise available from computer readable media. Such instructions can include, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can include hardware, firmware and/or software, and can take any of a variety of form factors. Typical examples of such form factors include laptops, smart phones, small form factor personal computers, personal digital assistants, rackmount devices, standalone devices, smart mirrors, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" refers to at least one of a set and indicates that one member of the set or multiple members of the set satisfy the claim. For example, claim language reciting "at least one of A and B" means A, B, or A and B.

What is claimed is:

1. A defibrillator which assesses cardio pulmonary resuscitation (CPR) carried out by a person on a subject and provides CPR feedback to the person, comprising:
   a biosignal measurement system configured to measure biosignals of the subject, determine when CPR is required and produce a CPR start signal and determine and when CPR is no longer required and to produce a CPR stop signal,
   a CPR measurement system configured to measure compression signals during CPR chest compressions by the person,
   a CPR assessment system connected to the biosignal measurement system to receive the CPR start signal and the CPR stop signal, connected to the CPR measurement system receive compression signals and configured to perform steps comprising:
      (i) receiving the CPR start signal and produce a first feedback signal,
      (ii) receiving compression signals measured during a first plurality of chest compressions by the person,
      (iii) using the compression signals to establish a first CPR performance measurement of the person,
      (iv) setting a CPR performance baseline of the person equal to the first CPR performance measurement of the person,
      (v) receiving compression signals measured during a further plurality of chest compressions by the person,
      (vi) using the compression signals to establish a further CPR performance measurement of the person,
      (vii) comparing the further CPR performance measurement of the person with the CPR performance baseline of the person,
      (viii) when the further CPR performance measurement of the person is greater than the CPR performance baseline of the person, producing a second feedback signal and set the CPR performance baseline of the person equal to the further CPR performance measurement of the person and go to step (x),
      (ix) when the further CPR performance measurement of the person is less than the CPR performance baseline of the person, producing a third feedback signal and go to step (x),
      (x) when the CPR stop signal is not received, returning to step (v), and
      (xi) when the CPR stop signal is received, producing a fourth feedback signal, and
   a feedback unit connected to the CPR assessment system and configured to receive the feedback signals and issue CPR feedback to the person.

2. A defibrillator according to claim 1, wherein steps (viii) to (x) further comprise:
   (viii) when the further CPR performance measurement is greater than the CPR performance baseline, producing the second feedback signal and set the CPR performance baseline equal to the further CPR performance measurement and go to step (x)(a),
   (ix) when the further CPR performance measurement is less than the CPR performance baseline, producing the third feedback signal and go to step (x)(b),
   (x)(a) when the CPR stop signal is not received, waiting for a plurality of chest compressions, return to step (v),
   (x)(b) when the CPR stop signal is not received, returning to step (v).

3. A defibrillator according to claim 1, wherein steps (ii) to (iv) further comprise:
   (ii) receiving first compression signals measured during a first plurality of chest compressions and at least second compression signals measured during a second plurality of chest compressions,
   (iii) using the first compression signals to establish a first CPR performance measurement and use the at least second compression signals to establish an at least second CPR performance measurement, and
   (iv) setting a CPR performance baseline equal to the greater of the first CPR performance measurement and the at least second CPR performance measurement.

4. A defibrillator according to claim 1, wherein steps (v) to (x) further comprise:
   (v)(a) setting a CPR counter equal to x,
   (v)(b) receiving compression signals measured during a further plurality of chest compressions,
   (vi) using the compression signals to establish a further CPR performance measurement,
   (vii) comparing the further CPR performance measurement with the CPR performance baseline,
   (viii) when the further CPR performance measurement is greater than the CPR performance baseline, produce the second feedback signal, setting the CPR performance baseline equal to the further CPR performance measurement and going to (x)(a),
   (ix)(a) when the further CPR performance measurement is less than the CPR performance baseline, when the CPR counter is not equal to zero, producing the third feedback signal, decreasing the CPR counter by 1 and going to (x)(b),
   (ix)(b) when the further CPR performance measurement is less than the CPR performance baseline, when the CPR counter is equal to zero, producing the second feedback signal, decreasing the CPR performance baseline and going to (x)(a), and
   (x)(a) when the CPR stop signal is not received, returning to step (v)(a), and
   (x)(b) when the CPR stop signal is not received, returning to step (v)(b).

5. A defibrillator according to claim 1, wherein step (ii) further comprises:
   (ii)(a) setting a CPR counter equal to x,
   (ii)(b) receiving compression signals measured during a first plurality of chest compressions,
   (ii)(c) receiving a compression rate measured during the first plurality of chest compressions to yield a measured compression rate,
   (ii)(d) comparing the measured compression rate with a minimum required compression rate,
   (ii)(e) when the measured compression rate is greater than the minimum required compression rate, going to step (iii),
   (ii)(f) when the measured compression rate is less than the minimum required compression rate, when the CPR counter is not equal to zero, decreasing the CPR counter by 1, producing a fifth feedback signal and going to step (ii)(b), and
   (ii)(g) when the measured compression rate is less than the minimum required compression rate, when the CPR counter is equal to zero, going to step (iii).

6. A defibrillator according to claim 1 wherein step (ii) further comprises:
   (ii)(a) setting a CPR counter equal to x,
   (ii)(b) receiving compression signals measured during a first plurality of chest compressions, (ii)(c) receiving a compression rate measured during the first plurality of chest compressions to yield a measured compression rate, (ii)(d) comparing the measured compression rate with a maximum required compression rate, (ii)(e) when the measured compression rate is less than the maximum required compression rate, going to step (iii), (ii)(f) when the measured compression rate is greater than the maximum required compression rate, when the CPR counter is not equal to zero, decreasing the CPR counter by 1, producing a sixth feedback signal and going to step (ii)(b), and (ii)(g) when the measured compression rate is greater than the maximum required compression rate, when the CPR counter is equal to zero, going to step (iii).

7. A defibrillator according to claim 1, wherein step (ii) further comprises:
(ii)(a) setting a CPR counter equal to x,
(ii)(b) receiving compression signals measured during a first plurality of chest compressions,
(ii)(c) receiving a compression rate measured during the first plurality of chest compressions to yield a measured compression rate,
(ii)(d) comparing the measured compression rate with a minimum required compression rate and a maximum required compression rate,
(ii)(e) when the measured compression rate is greater than the minimum required compression rate and when the measured compression rate is less than the maximum required compression rate, going to step (iii),
(ii)(f) when the measured compression rate is less than the minimum required compression rate, when the CPR counter is not equal to zero, decreasing the CPR counter by 1, producing a fifth feedback signal and going to step (ii)(b),
(ii)(g) when the measured compression rate is less than the minimum required compression rate, when the CPR counter is equal to zero, going to step (iii),
(ii)(h) when the measured compression rate is greater than the maximum required compression rate, when the CPR counter is not equal to zero, decreasing the CPR counter by 1, producing a sixth feedback signal and going to step (ii)(b), and
(ii)(i) when the measured compression rate is greater than the maximum required compression rate, when the CPR counter is equal to zero, going to step (iii).

8. A defibrillator according to claim 1, wherein step (v) further comprises:
(v)(a) setting a CPR counter equal to x,
(v)(b) receiving compression signals measured during a further plurality of chest compressions,
(v)(c) receiving a compression rate measured during the further plurality of chest compressions to yield a measured compression rate,
(v)(d) comparing the measured compression rate with a minimum required compression rate,
(v)(e) when the measured compression rate is greater than the minimum required compression rate, going to step (vi),
(v)(f) when the measured compression rate is less than the minimum required compression rate, when the CPR counter is not equal to zero, decreasing the CPR counter by 1, producing a fifth feedback signal and going to step (v)(b), and (v)(g) when the measured compression rate is less than the minimum required compression rate, when the CPR counter is equal to zero, going to step (vi).

9. A CPR feedback device according to claim 1, wherein step (v) further comprises:
(v)(a) setting a CPR counter equal to x,
(v)(b) receiving compression signals measured during a further plurality of chest compressions,
(v)(c) receiving a compression rate measured during the further plurality of chest compressions to yield a measured compression rate,
(v)(d) comparing the measured compression rate with a maximum required compression rate,
(v)(e) when the measured compression rate is less than the maximum required compression rate, going to step (vi),
(v)(f) when the measured compression rate is greater than the maximum required compression rate, when the CPR counter is not equal to zero, decreasing the CPR counter by 1, producing a sixth feedback signal and going to step (v)(b), and
(v)(g) when the measured compression rate is greater than the maximum required compression rate, when the CPR counter is equal to zero, going to step (vi).

10. A defibrillator according to claim 1, wherein step (v) further comprises:
(v)(a) setting a CPR counter equal to x,
(v)(b) receiving compression signals measured during a further plurality of chest compressions,
(v)(c) receiving a compression rate measured during the further plurality of chest compressions to yield a measured compression rate,
(v)(d) comparing the measured compression rate with a minimum required compression rate and a maximum required compression rate,
(v)(e) when the measured compression rate is greater than the minimum required compression rate and when the measured compression rate is less than the maximum required compression rate, going to step (vi),
(v)(f) when the measured compression rate is less than the minimum required compression rate, when the CPR counter is not equal to zero, decreasing the CPR counter by 1, producing a fifth feedback signal and going to step (v)(b),
(v)(g) when the measured compression rate is less than the minimum required compression rate, when the CPR counter is equal to zero, going to step (vi),
(v)(h) when the measured compression rate is greater than the maximum required compression rate, when the CPR counter is not equal to zero, decreasing the CPR counter by 1, producing a sixth feedback signal and going to step (v)(b), and
(v)(i) when the measured compression rate is greater than the maximum required compression rate, when the CPR counter is equal to zero, going to step (vi).

11. A defibrillator according to claim 1, in which the CPR assessment system is configured to perform a step (iii)(a) after step (iii) comprising:
comparing the first CPR performance measurement with a minimum CPR performance measurement, when the first CPR performance measurement is greater than the minimum CPR performance measurement, going to step (iv), and
when the first CPR performance measurement is less than the minimum CPR performance measurement, producing the third feedback signal and returning to step (ii).

12. A defibrillator according to claim 11, in which the CPR assessment system is configured to perform a step (iii)(b) after step (iii)(a) comprising:
  comparing the first CPR performance measurement with a maximum CPR performance measurement, when the first CPR performance measurement is less than the maximum CPR performance measurement, going to step (iv), and
  when the first CPR performance measurement is greater than the maximum CPR performance measurement, producing a seventh prompt signal and returning to step (ii).

13. A defibrillator according to claim 1, in which the CPR assessment system is configured to perform a step (vi)(a) after step (vi) comprising:
  comparing the further CPR performance measurement with a minimum CPR performance measurement, when the further CPR performance measurement is greater than the minimum CPR performance measurement, going to step (vii), and
  when the further CPR performance measurement is less than the minimum CPR performance measurement, producing the third feedback signal and returning to step (v).

14. A defibrillator according to claim 13, in which the CPR assessment system is configured to perform a step (vi)(b) after step (vi)(a) comprising:
  comparing the further CPR performance measurement with a maximum CPR performance measurement, when the further CPR performance measurement is less than the maximum CPR performance measurement, going to step (vii), and
  when the further CPR performance measurement is greater than the maximum CPR performance measurement, producing a seventh prompt signal and returning to step (v).

15. A defibrillator according to claim 1, in which the CPR measurement system measures compression signals during the first plurality of chest compressions and during the further plurality of chest compressions comprising displacement signals of the chest of the subject during the chest compressions.

16. A defibrillator according to claim 1, in which the CPR measurement system measures compression signals during the first plurality of chest compressions and during the further plurality of chest compressions comprising compression-sensitive physiological signals of the subject during the chest compressions.

17. A defibrillator according to claim 16, in which the compression-sensitive physiological signals of the subject consist of thoracic impedance signals.

* * * * *